(12) United States Patent
Sawatzki et al.

(10) Patent No.: US 7,601,364 B2
(45) Date of Patent: Oct. 13, 2009

(54) CARBOHYDRATE MIXTURES

(75) Inventors: Gunther Sawatzki, Munzenberg (DE); Bernd Stahl, Friedrichsdorf (DE)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 11/649,879

(22) Filed: Jan. 5, 2007

(65) Prior Publication Data

US 2007/0248649 A1 Oct. 25, 2007

Related U.S. Application Data

(63) Continuation of application No. 09/774,188, filed as application No. PCT/EP99/05878 on Aug. 11, 1999, now abandoned.

(30) Foreign Application Priority Data

Aug. 11, 1998 (DE) ................. 198 36 339

(51) Int. Cl.
*A61K 47/00* (2006.01)
*A01N 43/04* (2006.01)
*A61K 31/715* (2006.01)

(52) U.S. Cl. ........................ 424/439; 514/23; 514/53; 514/54

(58) Field of Classification Search ............ 424/439
See application file for complete search history.

(56) References Cited

U.S. PATENT DOCUMENTS

| | | | |
|---|---|---|---|
| 5,629,040 A | 5/1997 | Takemori et al. | |
| 5,733,579 A | 3/1998 | Wolf et al. | |
| 5,744,134 A | 4/1998 | Paul | |
| 5,776,887 A | 7/1998 | Wibert et al. | |
| 5,792,754 A | 8/1998 | Green et al. | |
| 5,840,361 A | 11/1998 | Theuer et al. | |
| 6,576,251 B1 * | 6/2003 | Stahl et al. .................. | 424/439 |

FOREIGN PATENT DOCUMENTS

| | | |
|---|---|---|
| AU | 1997/28718 | 7/1997 |
| EP | 0382355 | 8/1990 |
| EP | 0 511 761 A1 | 11/1992 |
| EP | 0307 523 B1 | 3/1993 |
| EP | 0593774 | 4/1994 |
| EP | 0 692 252 A1 | 1/1996 |
| EP | 0 705 539 A2 | 4/1996 |
| EP | 0 756 828 A | 2/1997 |
| EP | 0 958 825 A1 | 11/1999 |
| GB | 1305071 | 1/1973 |
| JP | 2-286058 A | 11/1990 |
| JP | 9-065855 A | 3/1997 |
| JP | 10-175867 A | 6/1998 |
| WO | WO 95/26646 | 10/1995 |
| WO | WO 96 13271 A | 5/1996 |
| WO | WO 97/02829 | 1/1997 |
| WO | WO 97/34615 | 9/1997 |
| WO | WO 98 26787 | 6/1998 |
| WO | WO 98/31241 * | 7/1998 |

OTHER PUBLICATIONS

Crittenden et al (Production, properties and applications of food-grade oligosaccharides. Trends in Food Science & Technologies, vol. 7, Nov. 1996. pp. 353-361).*
S. S. Cho et al., "Complex Carbohydrates in Foods", Marcel Dekker Inc., N. Y., 1999.
J. H. Cummings, "Gastrointestinal Effects of Food Carbodhydrate[1-3]", *Am J Clin Nutr*, Apr. 1995; Suppl. 4 61 (suppl): pp. 938-945.
T. Kohmoto et al., "Effect of Isomalto-oligosaccharides on Human Fecal Flora", *Bifidobacteria microflora*, vol. 7(2), pp. 61-69, 1988.
Masaki Ito et al., "Influence of Galactooligosaccharides on the Human Fecal Microflora", *J. Nutr. Sci. VItaminol*, 39, 635-640, 1993.
Masaki Ito et al., "Effects of Transgalactosylated Disaccharides on the Human Intestinal Microflora nd Their Metabolism", *J. Nutr. Sci. Vitaminol.*, 39, 279-288, 1993.
M. Roberfroid, "Dietary Fiber, Inulin, and Oligofructose: a review comparing their physiological effects", *Critical Reviews in Food Science and Nutricion*, 33(2): 103-148, 1993.
G. R. Gibson et al., "Dietary Modulation of the Human Colonic Mlcrobiota: Introducing the Concept of Prebiotics", *American Institute of Nutrition*, 0022-3166/1995, pp. 1401-1412.
G. R. Gibson et al., "Bifidogenic properties of different types of fructo-oligosaccharides", *Food Microbiology*, 1994, 11, pp. 491-498.
RAFTILOSE® P95 Product Sheet Release: May 1995.
RAFTILINE® ST Product Sheet Release: May 1995.
RAFTILINE® HP Product Sheet Release: May 1995.
K. Yazawa et al., "Search for Sugar Sources for Selective Increase of Bifidobacteria", *Bifidobacteria microflora*, vol. 1(1), pp. 39-44, 1982.
RAFTIMIX® 10 Product Sheet Release: May 1995.
Listing of sales of RAFTIMIX® 10 to clients i.a. iin period Sep. 13, 1996 to May 19, 1998, (1998).
Manufacture protocol with composition of RAFTIMIX® 10 1995.
Analysis of RAFTIMIX@10; RAFTIMIX® ST and RAFTILOSE® P95, (1995).

(Continued)

*Primary Examiner*—Jake M. Vu
(74) *Attorney, Agent, or Firm*—Gilberto M. Villacorta; Sunit Talapatra; Foley & Lardner LLP

(57) ABSTRACT

A carbohydrate mixture for dietetic foods and pharmaceuticals containing several carbohydrates is provided. The carbohydrate mixture comprises two different, substantially soluble carbohydrate components A and B, which remain undigested in the gastrointestinal tract and enter the large intestine without being resorbed. Component A comprises at least one monosaccharide, at least one oligosaccharide (disaccharide to hexasaccharide), or a mixture thereof. Component B comprises a polysaccharide or a mixture of two or more polysaccharides. Component A constitutes 5 to 95 wt-% and Component B constitutes 5 to 95 wt-% of the sum of the Components; and at least 80 wt-% of the carbohydrates/saccharides of Components A and B have a prebiotic effect. The inventive carbohydrate mixture exhibits not only a nutritive effect, but also stimulates health-promoting microorganisms present in the natural flora of the large intestine.

5 Claims, No Drawings

OTHER PUBLICATIONS

R. Hartemink "Non-digestible oligosaccharides: healthy food for the colon?" *Wageningen*, The Netherlands, 1997, p. 130-131.

E. Meleghi et al., XXI International Dairy Congress; brief communications "New baby food milk products", (1982).

R. Tanaka et al., "Effects of Administration of TOS and Bifodobacterium breve 4006 on the Human fecal flora",*Bifidobacteria microflora*, vol. 2(1), 17-24, 1983.

S. Salimen et al., "Functional food science and gastrointestinal physiology and function", *British Journal of Nutrition*, 1998, 80, Suppl. 1, S147-S171.

G. Gibson et al., "Dietary Modulation of the Human Colonic Microbiota: Introducing the Concept of Prebiotics", *American Institute of Nutrition*, pp. 1401-1412, 1995.

Y. Bouhnik et al., "Administration of Transgalacto-Oligosaccharides Increases Fecal Bifiobacteria and Modifies Colonic Fermentation Metabolism in Healthy Humans", *American Society for Nutritional Sciences*, pp. 444-448, 1997.

M. Ito et al., "Effects of Administration of Galactooligosaccharides on the Human Faecal Microflora, Stool Weight and Abdominal Sensation", *Microbial ecology in health and disease*, vol. 3, pp. 285-292, 1990.

R. G. Crittenden et al., "Production, properties and applications of food-grade oligosaccharides", *Trends in Food Science & Technologies*, vol. 7, Nov. 1996, pp. 353-361.

G. R. Gibson et al., "Selective stimulation of bifidobacteria in the Human Colon by Oligofructose and Inulin", *Gastroenterology* 1995, 108, pp. 975-982.

Haastrecht, "Oligosaccharides: Promising Performers in New Product Development," *IFI*, No. 1, 1995, pp. 23-27.

Frisomum, Analysis Chart and Brochure, 1998.

Ito, et al., "Influence of Lactose on Faecal Microflora in Lactose Maldigestors," *Microbial Ecology in Health and Disease*, vol. 6, 1993, pp. 73-76.

Hertzler, et al., "Colonic Adaptation to Daily Lactose Feeding in Lactose-Maldigesters Reduces Lactose-Intolerance," *Am. J. Clin. Nutr.*, 1996, pp. 232-236.

Mizota, et al., "Lactulose as a Sugar with Physiological Significance," *Bulletin IDF*, No. 212, Trends in Whey Utilization, 1987, Chapter 11.

Bernhart, et al, "Lactulose in Modified Milk Products for Infant Nutrition," *J. Dairy Sci.*, 1956, pp. 399-400.

Dombo, et al., "Production Health Benefits and Applications of Galacto-oligosaccharides," Yalpani M. ed., *New Technologies for Healthy Foods and Neutraceuticals*, ATL Press, Shewsbury, MA, 1997, pp. 143-156.

Jiang, et al., "In Vitro Lactose Fermentation by Human Colonic Bacteria is Modified by *lactobacillus* Acidophilus Supplementation," *American Society for Nutritional Sciences*, 1997, pp. 1489-1495.

RAFTILINE HP Product Sheet, May 1995.

Rotimi, et al, "The Development of the Bacterial Flora in Normal Neonates," 1981, pp. 51-61.

Rubaltelli, et al., "Intestinal Flora in Breast- and Bottle-fed Infants," 1998, pp. 186-190.

Roberfroid, et al., "Health Benefits of Non-Digestible Oligosaccharides," 1997.

Craig, et al., "Polydextrose as Soluble Fiber: Physiological and Analytical Aspects," 1998, pp. 370-376.

Terada, et al., "Effect of Lactosucrose on Fecal Flora and Fecal Putrefactive Products of Cats," 1993.

Mitsuoka, "Intestinal Flora and Human Health," *Asa Pacific J. Clin. Nutr.*, vol. 15, 1996, pp. 2-8.

Van Loo, et al., "On the Presence of Inulin and Oligofructose as Natural Ingredients in the Western Diet," *Critical Reviews in Food Science and Nutrition*, vol. 35, No. 6, 1995, pp. 525-552.

* cited by examiner

CARBOHYDRATE MIXTURES

This application is a continuation application of pending U.S. application Ser. No. 09/774,188, filed Mar. 20, 2001 (of which the entire disclosure of the pending prior application is hereby incorporated by reference), which is a 371 of PCT/EP99/05878, filed Aug. 11, 1999.

The invention relates to carbohydrate mixtures for dietetic foods and pharmaceuticals, dietetic and pharmaceutical compositions containing said carbohydrate mixtures, and to the use of said carbohydrate mixtures for stimulating the human large intestinal flora.

As is generally known, carbohydrates represent one of the essential foundations of nutrition. This is the reason why the most differing carbohydrates are admixed to the most differing foods and also to pharmaceuticals. The task of the carbohydrates therefore is primarily of the nutritive kind, and they serve as roughage respectively.

Carbohydrates consist of monosaccharides, and are respectively composed thereof. Depending on their polymerization degree, the carbohydrates are indicated as oligosaccharides or polysaccharides or glycans respectively. The carbohydrates thereby are present as free oligosaccharides, as well as in a bonded form such as for example in glycoproteins, proteoglycans and glycolipids.

Due to the variability of the monomers forming the carbohydrates, and due to the position of the glycosidic bond and the anomeric state of the carbohydrates and their conjugates, said carbohydrates and their conjugates represent an extremely heterogeneous and extensive substance class.

Carbohydrates have most differing biological functions. Thus, they influence, for example, the bacterial colonization of the large intestine, which is a prerequisite for its normal function. The microflora of the large intestine takes part in the intestinal functions in a very complex manner. This influence is preponderantly exercised by the fermentation of food components, which have not been resorbed in the small intestine. The fermentation encompasses a plurality of functions such as the further digestion of these food components, the detoxification of endogenously occurring metabolites, the synthesis of new metabolites, some of them having a very specific effect, the return resorption of bile acids, and many other processes. The normal microflora also has a health-promoting effect in that it suppresses the growth of other pathogenous microorganisms.

Bacteria, which produce lactic acid as their most important final metabolite (so-called lactic acid-producing bacteria), play an essential role as the important representatives of the normal microflora of the large intestine. Examples for this group are bacteria of the *lactobacillus* and *bifidobacterium* genus. Therefore, efforts have been undertaken for an extended period of time on ways to control the development of a lactic acid-dominant intestinal flora by means of dietetic measures. This is particularly important in cases when a normal intestinal flora is not present or not sufficiently present due to processes caused by the development such as, for example, of new born babies or due to pathogenous states such as, for example, subsequent to an enteral antibiotic therapy or another drug therapy or during and after enteral infections.

Carbohydrates are now increasingly used in food, "functional food" and pharmaceuticals under the aspect of a biological efficiency. Thus, it is, for example, known that some carbohydrates exercise a growth-promoting effect upon various species of *bifidobacteria*, but also upon *lactobacilli*. Thus, galacto oligosaccharides, for example, have a growth-promoting effect upon *lactobacillus casei*. To date, however, only very specific species of carbohydrates having determined properties are used for promoting certain biological actions.

Thus, WO 98/26787, for example, describes the use of β-glucan and compounds derived thereof for the promotion of the population of lactic acid-producing microorganisms in the gastrointestinal tracts of human beings and animals. Mixtures may also be used, which contain further prebiotic substances, the latter not being specified in detail.

Moreover, mixtures are known from WO 96/13271, which contain various oligosaccharides and polysaccharides apart from immunoglobulins. These mixtures are used as a dietetic supplement, which, with oral administration, is supposed to be active against various gastrointestinal pathogens. The saccharides used are thereby indicated as soluble dietetic fibre, whereby it concerns inulin, fructo-oligosaccharides, pectin, guar gum and mixtures thereof.

In EP 0 756 828 A1, fibre-containing nutrient compositions are described, which contain in addition to oligosaccharides and/or starch, soluble polysacchararides not representing starch and insoluble polysaccharides not representing starch.

It is the object of the present invention to provide improved carbohydrate mixtures, which may be incorporated in dietetic nutritions and pharmaceuticals, and which, in addition to their nutritive effect, also stimulate health-promoting microorganisms present in the natural flora of the large intestine.

This object is solved by means of carbohydrate mixtures according to the teaching of the present claims.

Thus, the carbohydrate mixtures according to the present invention, contain at least two different, essentially soluble carbohydrate components A and B, which remain undigested in the gastrointestinal tract and reach the large intestine unresorbed. The carbohydrate mixtures according to the present invention may also consist exclusively of these two carbohydrate components A and B.

Carbohydrate component A thereby consists of at least one monosaccharide or from at least one oligosaccharide. Oligosaccharides are thereby understood as those comprising of 2 to 7 monosaccharide units. Hence, the oligosaccharides refer to disaccharides, trisaccharides, tetrasaccharides, pentasaccharides and hexaasaccharides. Carbohydrate component A may also be formed by a compound of two or more of the mentioned saccharides. It may therefore be comprised of only one monosaccharide or of a mixture of two or more monosaccharides or of a mixture of one or more monosaccharide/s with one or more oligosaccharide/s. It may also be comprised of any arbitrary number of various monosaccharides and/or oligosaccharides of that kind.

Carbohydrate component B consists of at least one polysaccharide comprising 7 or more monosaccharide units. Polysaccharides are understood as those starting from heptasaccharide (e.g. heptasaccharide, oktasaccharide, nonasaccharide, decasaccharid, etc.). Carbohydrate component B, may also be comprised of only one polysaccharide of that kind or of any arbitrary number of polysaccharides of that kind.

Accordingly, when in the following or in the claims, a carbohydrate component A or B is mentioned, it may refer to any one of all of these variants.

Carbohydrate component A thereby represents up to 95 wt-% of the sum of carbohydrate component A and carbohydrate component B (A+B=100 wt-%). Carbohydrate component B represents 5 to 95 wt-% of the sum of carbohydrate component A and carbohydrate component B.

At least 80 wt-% of the carbohydrates or saccharides out of the sum of carbohydrate component A and B thereby have a prebiotic effect. Preferably, at least 80 wt-% of the carbohydrates belonging to carbohydrate component A, and also at least 80 wt-% of those belonging to carbohydrate component B, have a prebiotic effect. In other words, preferably at least 80 wt-% each of the carbohydrates or saccharides out of carbohydrate components A and B, are intended to reach the large intestine in an undigested (hence not resorbable in the small intestine) manner. In other words, these carbohydrates or saccharides of carbohydrate components A and B in the gastrointestinal tract are neither resorbed and digested in the stomach nor in the small intestine, but reach the large intestine as such.

The proportion of the not prebiotically active carbohydrates or saccharides of carbohydrate components A and B therewith amounts to a maximum of 20 wt-%. These carbohydrates or saccharides refer to those, which are actually soluble, but can be excreted in an undigested form. These carbohydrates can exercise a physical effect in that they increase, for example, the volume of the faeces or prompt a water adsorption.

Soluble carbohydrates in the sense of the present invention are understood as those, which form a homogenous solution in the physical sense in water, in a concentration of at least 1 g/l at room temperature (e.g. pursuant to Roempp's Chemie Lexikon).

Such as it has already been stated, the inventive carbohydrate mixtures may consist exclusively of the carbohydrate components A and B or may contain them. For the assessment of the proportion determining the carbohydrate components A and B in a dietary or pharmaceutical product, the following steps are carried out:

In a first stage, all soluble carbohydrates are extracted from the product by means of water. Fats and proteins are removed from the extract.

In a second stage, the soluble carbohydrates, or the extract respectively, are digested by means of human enzymes, e.g. human amylase, human pancreatic juice or a small intestine ciliated border preparations. The thereby resulting non-digested carbohydrates (except for the in-vivo-resorbable monosaccharides obtained in this in-vitro experiment), constitute the two carbohydrate components A and B, and 80% thereof are supposed to be prebiotically active.

A prebiotically active carbohydrate according to the present invention is understood as a carbohydrate, which reaches the large intestine undigested (and hence is not resorbable in the small intestine), and there, it selectively encourages the growth and/or the activity of one or of a restricted number of bacterial species in the intestine, and consequently promotes health. This prebiotic effect of such carbohydrates and their specific mechanisms are described in detail in "G. R. Gibson & M. B. Roberfroid, *J. Nutr.* 1995; 125: 1401-1412", whereto explicit reference is herewith made, and the disclosure of which is included in the present documents.

The inventive carbohydrate mixtures hence are those, wherein the carbohydrates, which are soluble and undigested in the sense described above, fulfill the herein specified criteria and constitute the carbohydrate components A and B.

Apart from these carbohydrate components A and B, other carbohydrates may be present as well. Amongst those are 1.) the actually soluble but digestible carbohydrates, which are digestible according to the above-described second stage, and 2.) the insoluble carbohydrates, which are resorbable./.digestible or even not resorbable./.digestible.

These carbohydrates enumerated sub 1.) and 2.), may be present as such in any arbitrary quantities in addition to the carbohydrate components A and B, in each case depending on the desired final product. Preferably, the insoluble carbohydrates constitute 0 to 10 wt-% of the carbohydrate mixtures.

Carbohydrate component A may, for example, consist of one or more of the following carbohydrates: β-galactooligosaccharides, α-galactooligosaccharides, fructo-oligosaccharides, fuco-oligosaccharides, manno-oligosaccharides, xylo-oligosaccharides, sialyl-oligosaccharides, N-glycoprotein oligosaccharides, O-glycoprotein oligosaccharides, glycolipid oligosaccharides, cello-oligosaccharides, chitosan-oligosaccharides, chitin-oligosaccharides, galacturono-oligosaccharides, glucurono-oligosaccharides, β-glucan oligosaccharides, arabinoxylo-oligosaccharides, arabinogalacto-oligosaccharides, xylogluco-oligosaccharides, galactomanno-oligosaccharides, rhamno-oligosaccharides.

Carbohydrate component B may, for example, be formed of one or more of the following carbohydrates or saccharides:

Soluble carbohydrates or saccharides: fruct(os)anes/inulins, galactans, fucoidans, arabinans, xylans, xanthans, β-glucans, galacturonans, N-glycans, O-glycans, hyaluronic acids, chondroitins, xyloglucans, arabinogalactans, alginates, carageenanes, galactomannans, arabinoxylanes, glycolipid glycans, glycoprotein glycans, proteoglycans.

By means of a selective combination of oligosaccharides and polysaccharides, and consequently the simultaneous presence of carbohydrate components A and B, the health-promoting microorganisms in the large intestine may be promoted by an essentially higher efficiency than it would be the case with only one of said carbohydrate components. Thus, it is possible with the administration of the inventive combination, to make very rapid restitution of a normal large intestinal flora, to maintain same or to prophylactically prevent an alteration of the intestinal flora during situations of stress, and thus to influence the bacterial colonization of the large intestine in a way, which is more efficient than the one with the previously used carbohydrates.

According to a preferred embodiment, at least 80 wt-% of carbohydrate component A as well as of carbohydrate component B consist of carbohydrates, which are bifidogenous and./.or which promote lactic acid bacteria. Due to such a combination of oligosaccharides and polysaccharides having said properties, the growth of the lactic acid bacteria may surprisingly be promoted in an essentially stronger manner than this would be the case with oligosaccharides or polysaccharides alone. Not only lactic acid bacteria are thereby promoted, which are naturally present in the intestine, but also the growth of those is promoted—optionally even in a selective manner—which are introduced exogenously.

Apart from this indirect action via the bacteria themselves and their metabolites such as fatty acids (butyrate, propionate, etc.), pH effects and stimulation of colonozytes, direct physical effects such as peristalsis, water content, quantity of faeces, mechanical action upon the intestinal mucosa are likewise positively influenced.

Thus, the inventive carbohydrate mixtures dispose not only of a nutritive effect but also of a wide spectrum of activities. In addition to the above-described biological effects, the following may also be achieved by means of the inventive mixtures: stabilization of a natural microflora, prevention of pathogenous substances./.organisms such as toxins, viruses, bacteria, fungi, transformed cells and parasites from adhering, dissolution of complexes of toxins, viruses, bacteria, fungi and other pathogens having endogenous cells, as well as their elimination from the body, and an acceleration of wound healing.

Thus, the inventive mixtures are suitable for the prophylaxis and/or the treatment of symptoms/diseases occurring in conjunction with a disturbed intestinal flora, for example, as a consequence of the association./.adhesion of the mentioned substances and organisms with/on epithelia or other endogenous cells.

The carbohydrates or saccharides of carbohydrate components A and B primarily differ in size. Nevertheless, mixtures have found to be particularly efficient, wherein the carbohydrates or the saccharides of carbohydrate component A, on the one hand, and of carbohydrate component B, on the other hand, are of a different structure. This different structure may, for example, concern the monosaccharide composition when, for example, fructans are used on the one hand, and galactans, on the other hand. This different structure may likewise concern the glycosidic bonding (e.g. α-galacto oligosaccharaides versus β-galacto oligosaccharaides or α-glucans (starch) versus β-glucans (cellulose)). The monomer composition, as well as the glycoside bonding may have an influence on the chemical behaviour (e.g. solubility) or on the physiological behaviour e.g. digestibility).

The core of the inventive mixtures may inter alia be seen in that carbohydrates of different sizes are used, which preferably and additionally belong to at least two different "classes". With an administration of such mixtures, a synergetic effect may occur relative to the prebiotic effects of the separate substance groups A and B.

Thus, the carbohydrates of component A may not belong to one substance class alone but may also be formed out of several classes (for example A: galacto-oligosaccharides plus fuco-oligosaccharides), whereas the carbohydrates of component B may equally originate from one substance class and also from several substance classes (for example B: inulins plus xylans).

According to a further preferred embodiment, the carbohydrate component A constitutes 95 to 60 wt-%, and in particular about 90 wt-%, and the carbohydrate component B 5 to 40 wt-%, and in particular about 10 wt-% of the carbohydrates present in toto.

Particularly efficient mixtures are those wherein at least 60 wt-%, and in particular 80 to 100 wt-% of the carbohydrates of carbohydrate component A belong to the group of the galacto-oligosaccharides, and at least 60 wt-%, and in particular 80 to 100 wt-% of the carbohydrates of carbohydrate component B belong to the group of the fructo-polysaccharides. Galacto-oligosaccharides are composed of galactose residues of different glycosidic bonds, in particular at the β 1-4 and β 1-6 position. At the reducing end, at β 1-4 of a glycosidic bond, glucose can be present. Fructo-polysaccharides, fructans, inulins and levans being part thereof, are composed of fructose residues of glycosidic bonds at the β 2-1 and β-6 position. At the reducing end, at β 2-1 of a glycosidic bond, glucose can be present.

When a range is mentioned within the scope of the present invention, said range indication will encompass and disclose at least all integral intermediate values, and even all narrower ranges embraced by the wider range. This means that for carbohydrate component A as well as for carbohydrate component B, which may both constitute 5 to 95 wt-%, that all intermediate values such as 6, 7, 8, 9 . . . 13, 14 . . . 25, 26, 27 . . . 30, 31, 32, 33 . . . 38, 39, 40, 41 . . . 47, 48, 49, 50, 51 . . . 59, 60, 61, 62, 63 . . . 72, 73, 74 . . . 79, 80, 81, 82 . . . 87, 88, 89, 90, 91, 92, 93 and 94 wt-% are likewise covered. The same applies to the indication that at least 80 wt-% of the carbohydrates of carbohydrate component A and at least 80 wt-% of the carbohydrates of carbohydrate component B are prebiotically active or promote lactic acid bacteria and/or are bifidogenic. Thus, the term "at least 80 wt-%" designates at least all single values between 80 wt-% and 100 wt-%, and hence, for example, 81, 82, 83, 84, 85, 86, 87, 88, 89, 90, 91, 92, 93, 94, 95, 96, 97, 98, 99 and 100 wt-%. The carbohydrate components A and B may therewith exclusively consist of such carbohydrates.

The mixing ratio between carbohydrate component A and carbohydrate component B hence is 5 to 95 wt-%, or 95 to 5 wt-% respectively, and in particular 95 to 60, or 5 to 40 wt-% respectively. Thus, at least all integral narrower ranges are disclosed as well. The weight ratio between carbohydrate component A and carbohydrate component B may therefore, for example, be 50:50, 51:49, 52:48, 53:47, 54:46, 55:45, 56:44, 57:43, 58:42, 49:41, 60:40, 61:39, 62:38, 63:37, 64:36, 65:35, 66:34, 67:33, 68:32, 69:31, 70:30, 71:29, 72:28, 73:27, 74:26, 75:25, 76:24, 77:23, 78:22, 79:21, 80:20, 81:19, 82:18, 83:17, 84:16, 85:15, 86:14, 87:13, 88:12, 89:11, 90:10, 91:9, 92:8, 93:7, 94:6, and 95:5.

The molecular weight of the polysaccharides may thereby be of some MDas, and may be extended to particular carbohydrates. Preferably, however, polysaccharide molecules are used comprising up to 100 monosaccharide units.

For the production of the inventive carbohydrate mixtures, carbohydrates and carbohydrate mixtures known to date and used in particular for the production of foods or food products can be used. It is also possible to use raw materials previously modified in a technical way. The preparation of the inventive mixtures may thereby ensue by means of a simple blending of the correspondingly selected carbohydrates or oligosaccharides with polysaccharides or the carbohydrate mixtures. The initial components must thereby be so mixed with one another that the inventive parameters are respected with the finished inventive mixtures.

As raw materials may be used reserve carbohydrates (fructans, galacto-oligosaccharides from legumes, fucoidan, α-glucane, laminarin, carragenan, mannans, galactomannans, agar), natural gum, N-glycosidic bonded carbohydrates of glycoproteins, O-glycosidic bonded carbohydrates of glycoproteins, glycans of glycolipids, enzymaticly prepared carbohydrates (galacto-oligosaccharides, gluco-oligosaccharides, xylo-oligosaccharides), bacterial carbohydrates (such as xanthans), as well as oligosaccharides (galacto-oligosaccharides, gluco-oligosaccharides (from α 1-2 and α 1-3 glucose residues), xylo-oligosaccharides), as well as skeletal carbohydrates such as celluloses, hemicelluloses (arabinans, galactans), pectins and chitins may be used. The substances should preferably be of food-grade (cf. Complex Carbohydrates in Foods, British Nutrition Foundation; Chapman & Hall, London 1990). It is also possible to carrying out an enzymatic modification of the raw materials by means of hydrolases (e.g. glycosidases, transglycosidases and lipases), transferases, isomerases (e.g. aldolases and ketolases), oxidoreductases (e.g. oxidases) and reductases (e.g. glucosedehydrogenases), lyases (e.g. polysaccharide lyases) and ligases of the raw materials and products. Moreover, it is possible to carry out a technical modification of the raw materials and products, namely by means of pressure (e.g. extrusion), temperature (e.g. caramelization), organic syntheses, organic modification (e.g. carboxymethylation and peracetylation), acid and/or alkaline hydrolysis and fractionation (e.g. depending on size and/or physico-chemical parameters such as charge and hydrophobicity).

The inventive carbohydrate mixtures thereby are essentially composed of the hereinafter listed monosaccharides and of the thereof composed oligosaccharides and polysaccharides: D-glucose, D-fructose, D-galactose, D-mannose, L-fucose, D-N-acetylglucosamine, D-N-acetylgalactosamine, D-xylose, L-rhamnose, D-arabinose, D-allose, D-talose, L-idose, D-ribose, as well as monosaccharides comprising carboxyl groups such as D-galacturon acid, D-glucuron acid, D-mannuron acid and/or the methylated forms thereof such as N-acetyineuramin acid, N-glycolyl-neuramin acid and/or the O-acetylated forms thereof.

Moreover, these monomers and the thereupon based higher units can be modified by means of $-OSO_3H$ groups and/or $-OPO_3H$ groups.

The subject matter of the present invention is also dietetic or pharmaceutical compositions containing said inventive carbohydrate mixtures, and the use of said above-described carbohydrate mixtures for promoting the flora of the large intestine in humans. The term "promoting/promotion" represents a general term for all of the above-listed biological actions. Thereto belongs in particular the promotion of the growth of lactic acid-producing bacteria.

The inventive mixtures may be present in the following products:

Formulas for prematurely born babies, formulas for maturely born babies, infant formulas, human milk fortifier, clinical nutrition (in general, the inventive mixture may replace a part or the entirety of other components in these nutritions, such as, for example, lactose, maltodextrin or starch, or may be added to the nutrition), pharmaceuticals, dietetic supplement (as sachet in drinks).

In the following, carbohydrate mixtures representing various preferred embodiments are described. The indications thereby refer to weight percent, if not indicated otherwise. In these examples it is stated to which carbohydrate components A or B the used carbohydrates belong. The carbohydrate component A is thereby only called "A", and carbohydrate component B only "B".

EXAMPLE 1

Composition
90% A=galacto-oligosaccharides
transgalacto-oligosaccharides, e.g. Elixor® (Company Borculo, enzymatic from lactose by means of β-galactosidase)
10% B=inulin
Inulin, e.g. Raftiline® HP (Company Orafti, extraction from chicories, physical separation of the low-molecular oligosaccharides)

For the preparation of the transgalacto-oligosaccharides (Elixor®), lactose is treated with β-galactosidase. The lactose is thereby catalytically transformed in galacto-oligosaccharides, whereby a plurality of galacto-oligosaccharides are formed having varying chain lengths. Primarily, disaccharides and trisaccharides comprising 3 or 2 galactose units are thereby obtained.

EXAMPLE 2

Composition
60% A=galacto-oligosaccharides
transgalacto-oligosaccharides (enzymatic from lactose by means of β-galactosidase)
40% B=inulin
Inulin, e.g. Raftiline® HP (Company Orafti, extraction from chicories, physical separation of the low-molecular oligosaccharides)

EXAMPLE 3

Composition
90% A=galacturon acid oligosaccharides
enzymatic from pectin
10% B=xylose polysaccharides
enzymatic from xylan (vegetable hemicellulose)

EXAMPLE 4

Composition
90% A=fructo-oligosaccharides
enzymatic from inulin by means of endo-inulinase
10% B=cellulose polysaccharides
enzymatic from cellulose by means of cellulase

EXAMPLE 5

Composition
90% A=galacto-oligosaccharides
10% B=arabinans
enzymatic from vegetable hemicellulose

EXAMPLE 6

Composition
55% A=galacto-oligosaccharides
45% B=fructo-polysaccharides

EXAMPLE 7

Composition
85% A=galacturon acid oligosaccharides
15% B=fructo-polysaccharides

EXAMPLE 8

Composition
90% A=gluco-oligosaccharides
enzymatic by means of glucosyltransferase
10% B=fructo-polysaccharides

EXAMPLE 9

Composition
90% A=fuco-oligosaccharides
enzymatic from algae fucoidan
10% B=fructo-polysaccharides

EXAMPLE 10

Composition
90% A=galacto-oligosaccharides
10% B=fuco-polysaccharides
enzymatic from algae fucoidan

EXAMPLE 11

Composition
55% A=galacto-oligosaccharides
α-galacto-oligosaccharides from soya
45% B=fructo-polysaccharides (inulin)

EXAMPLE 12

Composition
80% A=transgalacto-oligosaccharaides
10% A=galacturon acid oligosaccharides
10% B=inulin

The invention claimed is:

1. A carbohydrate mixture for dietetic foods and pharmaceuticals comprising at least two soluble carbohydrate components A and B, which remain undigested in the gastrointestinal tract and enter the large intestine without being resorbed,
   carbohydrate component A comprising oligosaccharides having 2 to 6 monosaccharide units, 80 to 100 weight percent of which oligosaccharides are galacto-oligosaccharides, and
   carbohydrate component B comprising polysaccharides having 7 or more monosaccharide units, 80 to 100 weight percent of which polysaccharides are fructo-polysaccharides,
   wherein the mixture comprises about 90 weight percent of carbohydrate component A and about 10 weight percent carbohydrate component B based on the sum of the carbohydrate components A+B.

2. The carbohydrate mixture according to claim 1, wherein at least 80 weight percent of the carbohydrates of carbohydrate components A and B promote lactic acid bacteria and/or are bifidogenic.

3. The carbohydrate mixture according to claim 1, wherein the carbohydrates of carbohydrate components A and B do not have any glucose units linked at the $\alpha$ 1-4 and/or $\alpha$ 1-6 position.

4. The carbohydrate mixture according to claim 1, wherein the carbohydrates of the component B are composed of a maximum of up to 100 monosaccharide units.

5. The carbohydrate mixture according to claim 1, further comprising an insoluble carbohydrate, a soluble and digestible carbohydrate, or a mixture thereof.

* * * * *